United States Patent
Sakaida

(10) Patent No.: US 6,704,591 B2
(45) Date of Patent: Mar. 9, 2004

(54) METHOD, APPARATUS AND PROGRAM FOR RESTORING PHASE INFORMATION

(75) Inventor: Hideyuki Sakaida, Kaisei-machi (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 0 days.

(21) Appl. No.: 10/413,511

(22) Filed: Apr. 15, 2003

(65) Prior Publication Data
US 2003/0199752 A1 Oct. 23, 2003

(30) Foreign Application Priority Data
Apr. 23, 2002 (JP) ........................... 2002-120735

(51) Int. Cl.$^7$ ............................... A61B 5/05
(52) U.S. Cl. ................. 600/407; 378/62; 378/43; 382/132
(58) Field of Search ................ 600/407, 410, 600/419, 420; 382/132; 378/37, 43, 62

(56) References Cited

U.S. PATENT DOCUMENTS

| | | | |
|---|---|---|---|
| 6,226,353 B1 | * | 5/2001 | Wilkins et al. ............ 378/98.9 |
| 6,262,818 B1 | * | 7/2001 | Cuche et al. ................ 359/9 |
| 2002/0176615 A1 | * | 11/2002 | Ito ............................ 382/132 |

OTHER PUBLICATIONS

Allman, Brendan E., et al., Noninterometric Quantitatie Phase Imaging With Soft Xrays, J. OPT. Soc. Am, Vol 17, N.10, Oct. 2000, pp. 1732–1743.

Gureyev Timur E., et al., Hard X–Ray Quantitative Non-–Interferometric Phase–Contrast Imaging, SPIE, Vol 3659 (1999), pp. 356–364.

* cited by examiner

Primary Examiner—Dennis Ruhl
Assistant Examiner—Barry Pass
(74) Attorney, Agent, or Firm—Sughrue Mion, PLLC

(57) ABSTRACT

In a phase information restoring method using a phase contrast method, the estimated accuracy of phase is enhanced. The phase information restoring method of restoring phase information of radiation transmitted through an object on the basis of a plurality of image signals respectively obtained by detecting intensity of radiation transmitted through the object on a plurality of planes different in distance from the object, comprises the steps of: obtaining a differential signal representing difference between a first image signal and a second image signal; subjecting any one of the plurality of image signals to a suppressing process or a removing process for high spatial frequency components thereof so as to generate a third image signal; obtaining Laplacian of phase with respect to the differential signal and the third image signal; and restoring phase information by applying an inverse Laplacian operation to the Laplacian of phase.

3 Claims, 8 Drawing Sheets

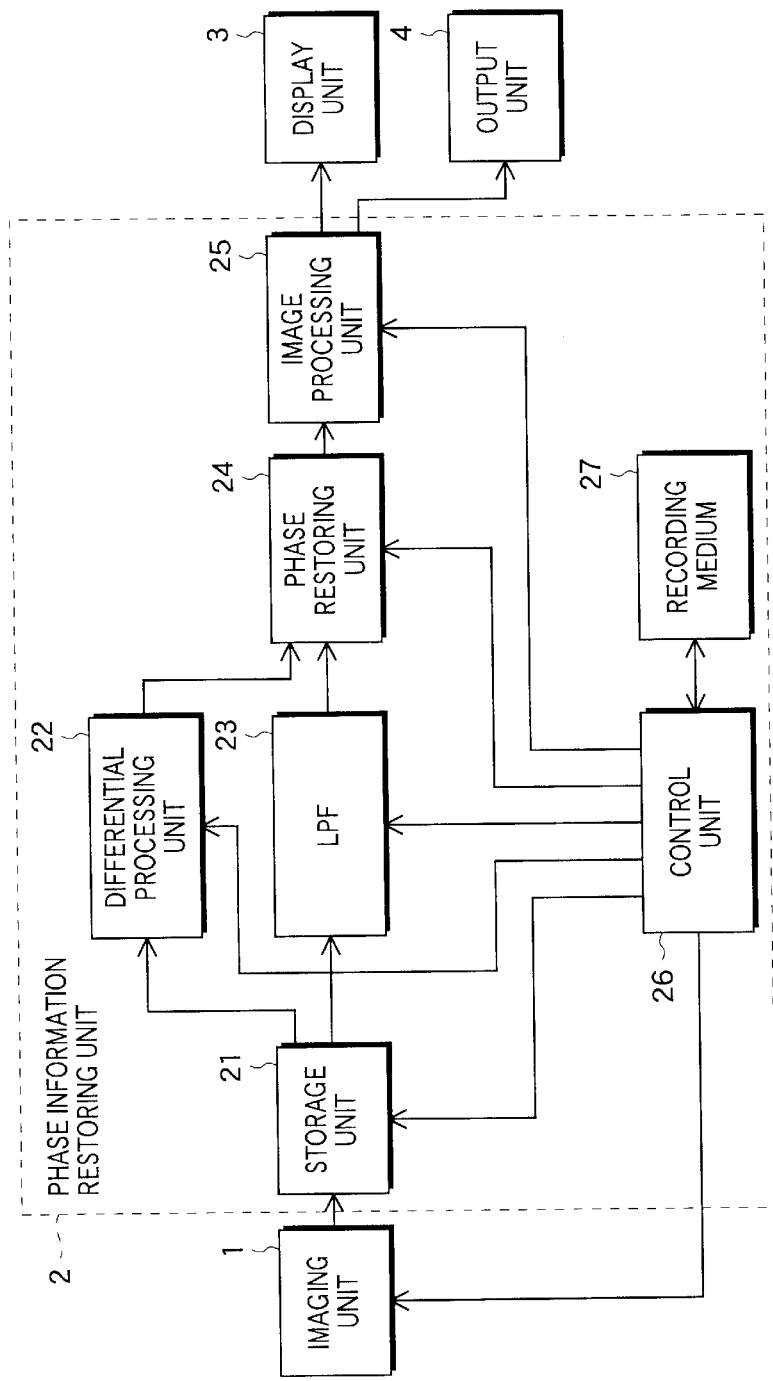

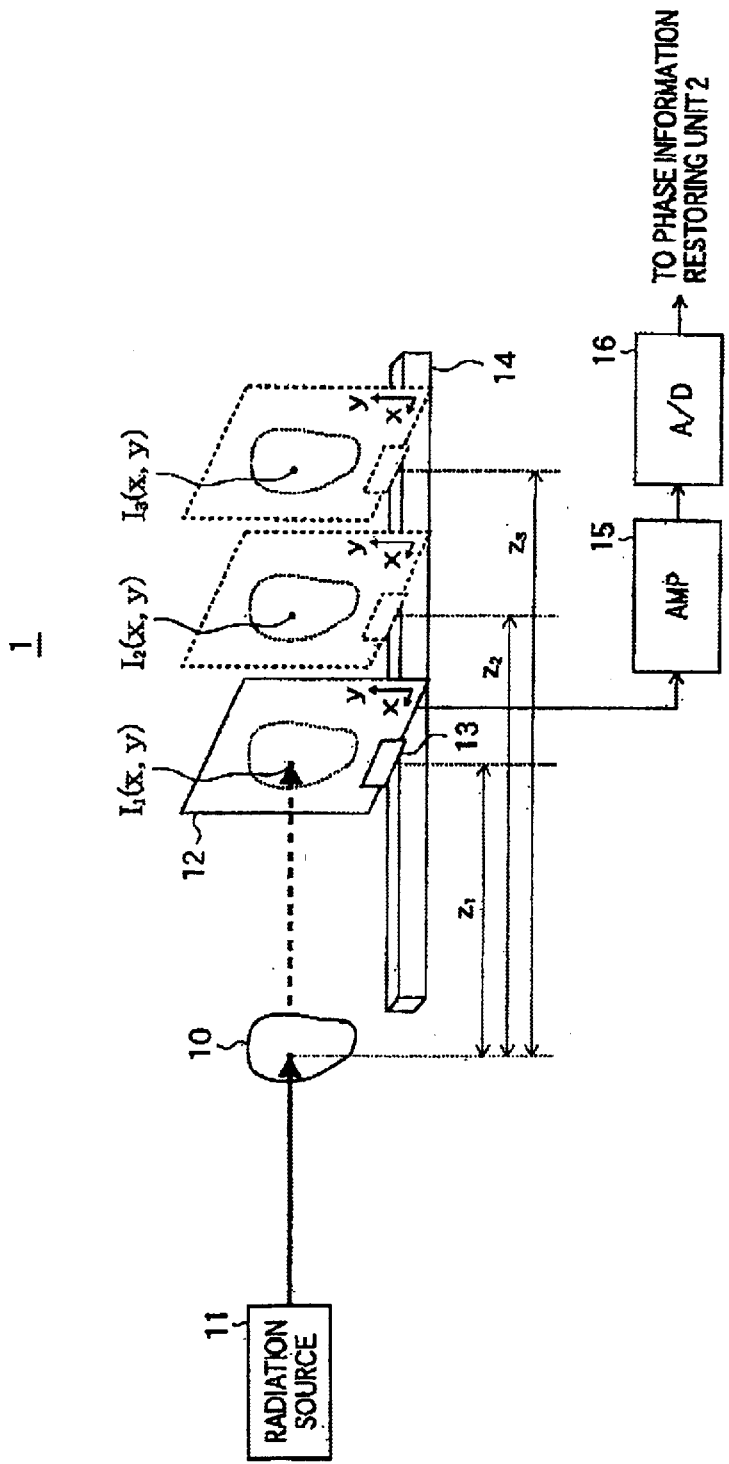

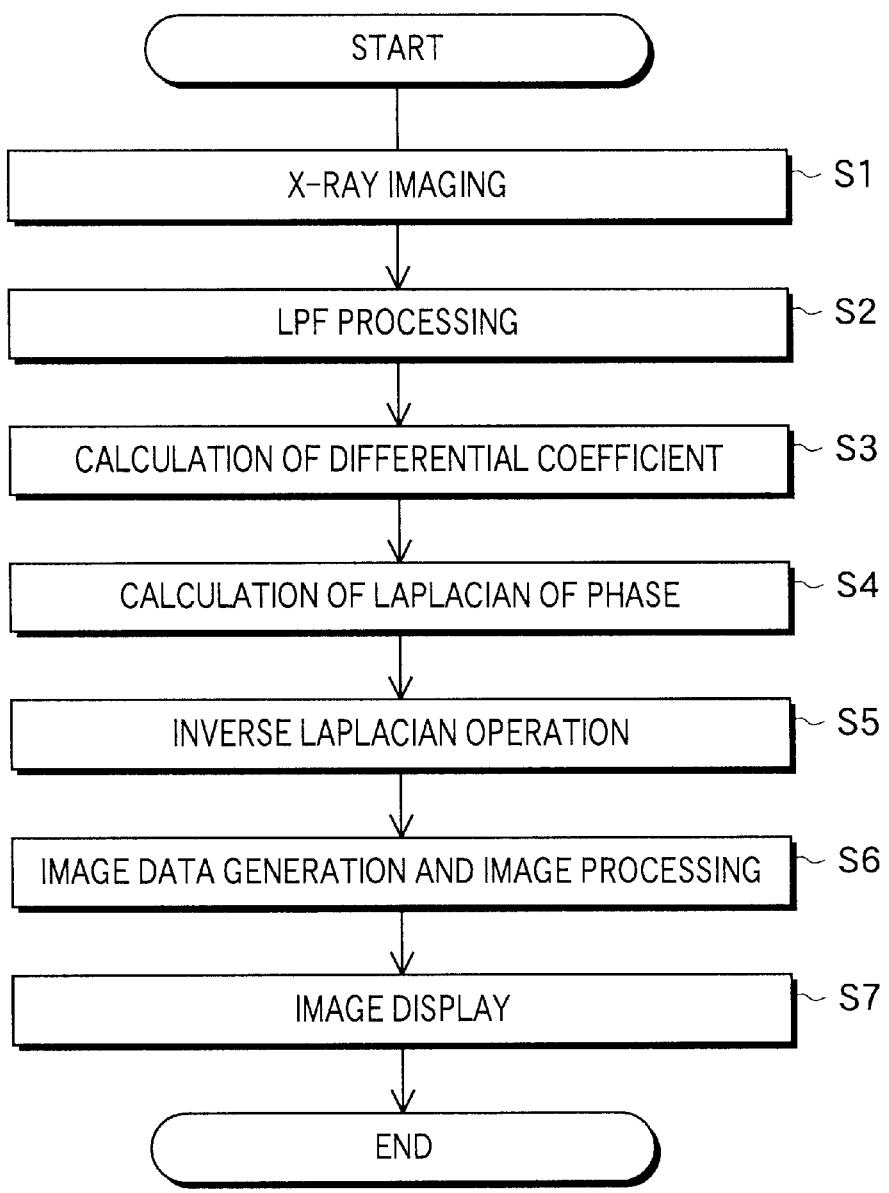

FIG.4A
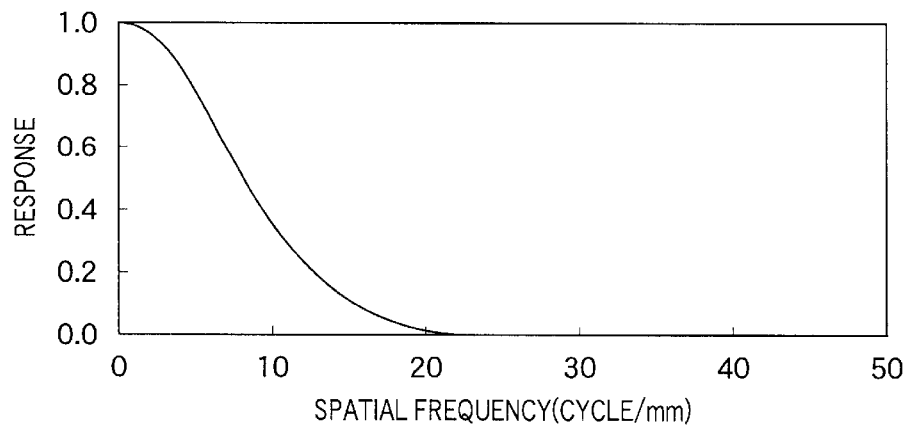
FIG.4B
| I(0) | I(1) | I(2) | I(3) | ... | I(N-2) | I(N-1) |
FIG.4C
| I'(0) | I'(1) | I'(2) | I'(3) | ... | I'(N-2) | I'(N-1) |
FIG.4D
| fil(0) | fil(1) | fil(2) | fil(3) | ... | fil(N-2) | fil(N-1) |
FIG.4E
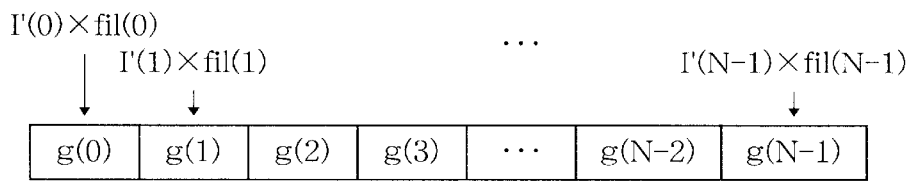

| I(0) | I(1) | I(2) | I(3) | ⋯ | I(N-2) | I(N-1) |

| fil'(-M+1) | fil'(-M+2) | ⋯ | fil'(-1) | fil'(0) | fil'(1) | ⋯ | fil'(M-2) | fil'(M-1) |

| 0.03 | 0.21 | 0.67 | 1.00 | 0.67 | 0.21 | 0.03 |

| 0.01 | 0.075 | 0.24 | 0.35 | 0.24 | 0.075 | 0.01 |

0.01+0.075+0.24+0.35+0.24+0.075+0.01=1

METHOD, APPARATUS AND PROGRAM FOR RESTORING PHASE INFORMATION

BACKGROUND OF THE INVENTION

1. Field of the Invention

The present invention relates to a method, an apparatus and a program for restoring phase information, which are used for constituting an image on the basis of image information obtained by radiation imaging or the like. In this application, the word "radiation" is used in a wide sense so as to include a corpuscular beam such as an electron beam, or an electromagnetic wave, in addition to a general radiation including X-rays and the like.

2. Description of a Related Art

Conventionally, an imaging method using X-rays or the like is utilized in various fields, and employed as one of the most important means for diagnosis, particularly, in a medical field. Since a first X-ray photograph was realized, X-ray photography has been repeatedly improved and a method using a combination of a fluorescent screen and an X-ray film is predominantly used at present. On the other hand, in recent years, various digitized devices such as X-ray CT, ultrasonic or MRI are in practical use and establishment of a diagnostic information processing system and the like in hospitals is being promoted. As for X-ray images, many studies have also been made for digitizing an imaging system. The digitization of the imaging system not only enables a long-term preservation of a large amount of data without incurring deterioration in image quality but also contributes to development into the medical diagnostic information system.

Incidentally, thus obtainable radiation images are generated by converting intensity of radiation transmitted through an object into brightness of the image. For example, in the case of imaging a region including a bone part, the radiation transmitted through the bone part is largely attenuated, and the radiation transmitted through a region other than the bone part, namely, a soft part is slightly attenuated. In this case, since the difference in the intensity of the radiation transmitted through different tissues is large, the radiation image with high contrast can be obtained.

On the other hand, for example, in the case of imaging a region of the soft part such as a breast, since the radiation apt to transmit wholly in the soft part, the difference between tissues in the soft part hardly appears as the difference in the intensity of the transmitted radiation. Because of this, as for the soft part, only a radiation image with low contrast can be obtained. Thus, the radiation imaging method is not suitable as a method of visualizing slight difference between tissues in the soft part.

Herein, information contained in radiation transmitted through an object includes phase information in addition to intensity information. In recent years, a phase contrast method has been studied in which an image is generated by using the phase information. The phase contrast method is an image construction technique for converting the phase difference resulted by transmitting X-rays or the like through the object into the brightness of the image.

Examples of the phase contrast method include a method of obtaining the phase difference on the basis of interference light generated by using an interferometer or a zone plate, and a method of obtaining the phase difference on the basis of diffracted light. Among them, in the method of obtaining the phase difference on the basis of the diffracted light, which method is called as a diffraction method, the phase difference is obtained on the basis of the following principle. For example, X-ray propagates through substance by travel of waves similar to light. Propagation velocity thereof varies depending on a refractive index of the substance. Therefore, when X-rays having a uniform phase are irradiated toward an object to be inspected, a difference is made in a propagation way of the X-ray, depending on the difference between tissues in the object. For this reason, a wave front of the X-ray transmitted through the object is distorted and, as a result, diffraction fringes are produced on an X-ray image obtained on the basis of the transmitted X-ray. A pattern of the diffraction fringes varies depending on the distance between a screen on which the X-ray image is formed and the object, or wavelength of the X-ray. Accordingly, by analyzing two or more sheets of X-ray images having different diffraction fringe patterns, phase difference of X-rays, which is produced at each position of the screen, can be obtained. By converting the phase difference into the brightness, the X-ray image, in which difference between tissues in the object clearly appears, can be obtained.

In particular, in the radiation transmitted through a soft part of an object, the phase difference is larger than the intensity difference depending on the difference of tissues through which the radiation has transmitted, and therefore, delicate difference between tissues can be visualized by using the phase contrast method.

For the purpose of using such a phase contrast method, imaging conditions in the radiation imaging or techniques for restoring the phase from the diffraction fringe pattern are being studied.

For example, B. E. Allman et al. "Noninterferometric quantitative phase imaging with soft x rays", J. Optical Society of America A, Vol. 17, No. 10 (October 2000) pp. 1732–1743 discloses that the phase restoration is performed on the basis of image information obtained by imaging with soft X-rays to constitute an X-ray image.

In this reference, TIE (transport of intensity equation), which is the basic equation of the phase restoration, is used.

$$k\frac{\partial I(\vec{r})}{\partial z} = -\nabla_\perp \cdot \{I(\vec{r})\nabla_\perp \phi(\vec{r})\} \quad (1)$$

where $$\nabla_\perp = \left(\frac{\partial}{\partial x}, \frac{\partial}{\partial y}\right)$$

and k is a wave number.

Here, principle of the phase restoration is described by referring to FIG. 8. As shown in FIG. 8, the X-ray having wavelength of λ emits from the left side of the figure, transmits through an object plane 101 and enters a screen 102 at a distance of z from the object plane 101. At this time, when assuming intensity of the X-ray and phase thereof at a position (x,y) on the screen 102 to be I (x,y) and φ (x,y) respectively, relationship represented by the following expression holds between the intensity I (x,y) and the phase φ (x,y). Here, the intensity I is square of amplitude of the wave.

$$\frac{2\pi}{\lambda}\frac{\partial I(x,y)}{\partial z} = -\nabla \cdot \{I(x,y)\nabla\phi(x,y)\} \quad (2)$$

In the expression (2), by substituting k=2π and rewriting (x,y) component into a vector r, the TIE represented by the expression (1) is derived.

Further, T. E. Gureyev et al. "Hard X-ray quantitative non-interferometric phase-contrast imaging", SPIE Vol. 3659 (1999) pp. 356–364, discloses that the phase restoration is performed on the basis of image information obtained by imaging with hard X-rays to constitute an X-ray image.

In this reference, the TIE represented by the expression (1) is approximated as follows.

First, the expression (1) is developed as follows:

$$-\kappa\frac{\partial I(x,y)}{\partial z} = \left(\frac{\partial}{\partial x}, \frac{\partial}{\partial y}\right) \cdot \left(I(x,y)\frac{\partial\phi(x,y)}{\partial x}, I(x,y)\frac{\partial\phi(x,y)}{\partial y}\right) \quad (3)$$

$$= \frac{\partial}{\partial x}\left(I(x,y)\frac{\partial\phi(x,y)}{\partial x}\right) + \frac{\partial}{\partial y}\left(I(x,y)\frac{\partial\phi(x,y)}{\partial y}\right)$$

$$= I(x,y)\left(\frac{\partial^2\phi(x,y)}{\partial x^2} + \frac{\partial^2\phi(x,y)}{\partial y^2}\right) +$$

$$\frac{\partial I(x,y)}{\partial x}\frac{\partial\phi(x,y)}{\partial x} + \frac{\partial I(x,y)}{\partial y}\frac{\partial\phi(x,y)}{\partial y}$$

$$= I(x,y)\nabla^2\phi(x,y) + \nabla I(x,y) \cdot \nabla\phi(x,y)$$

where $$\nabla^2 = \frac{\partial^2}{\partial x^2} + \frac{\partial^2}{\partial y^2}$$

Further, in the expression (3), the vector r in the above document is rewritten into (x,y) components.

When the second term of the right side in the expression (3) is approximated to zero, an approximate expression represented by the following expression (4) is obtained.

$$\frac{\partial I(x,y)}{\partial z} \cong -\frac{I(x,y)}{\kappa}\nabla^2\phi(x,y) \quad (4)$$

In the expression (4), φ(x,y) can be obtained from I(x,y) by a solving method such as the finite-element method.

However, in such the approximate expression (4), there is a problem that when I(x,y) has high spatial frequency components, estimated accuracy of the phase φ(x,y) is deteriorated.

SUMMARY OF THE INVENTION

The present invention has been accomplished to solve the above-mentioned problems. A first object of the present invention is to provide a phase information restoring method capable of enhancing estimated accuracy of the phase upon constituting a radiation image by a phase contrast method. A second object of the present invention is to provide a phase information restoring apparatus and a phase information restoring program for performing such a phase information restoring method.

A phase information restoring method according to the present invention is a method of restoring phase information of radiation transmitted through an object on the basis of a plurality of image signals respectively obtained by detecting intensity of radiation transmitted through the object on a plurality of planes different in distance from the object, each of the plurality of image signals representing radiation image information on the plurality of planes, the method comprising the steps of: obtaining a differential signal representing difference between a first image signal and a second image signal of the plurality of image signals; subjecting any one of the plurality of image signals to one of a suppressing process and a removing process for high spatial frequency components thereof so as to generate a third image signal; obtaining Laplacian of phase with respect to the differential signal and the third image signal; and restoring phase information of the radiation by applying an inverse Laplacian operation to the Laplacian of phase.

A phase information restoring apparatus according to the present invention is an apparatus for restoring phase information of radiation transmitted through an object on the basis of a plurality of image signals respectively obtained by detecting intensity of radiation transmitted through the object on a plurality of planes different in distance from the object, each of the plurality of image signals representing radiation image information on the plurality of planes, the apparatus comprising: differential signal generating means for obtaining a differential signal representing difference between a first image signal and a second image signal of the plurality of image signals; signal processing means for subjecting any one of the plurality of image signals to one of a suppressing process and a removing process for high spatial frequency components thereof so as to generate a third image signal; phase restoring means for obtaining Laplacian of phase with respect to the differential signal and the third image signal, and restoring phase information of the radiation by applying an inverse Laplacian operation to the Laplacian of phase.

A phase information restoring program according to the present invention is a phase information restoring program for restoring phase information of radiation transmitted through an object on the basis of a plurality of image signals respectively obtained by detecting intensity of radiation transmitted through the object on a plurality of planes different in distance from the object, each of the plurality of image signals representing radiation image information on the plurality of planes, the program actuating a CPU to execute the procedures of: obtaining a differential signal representing difference between a first image signal and a second image signal of the plurality of image signals; subjecting any one of the plurality of image signals to one of a suppressing process and a removing process for high spatial frequency components thereof so as to generate a third image signal; obtaining Laplacian of phase with respect to the differential signal and the third image signal; and restoring phase information of the radiation by applying an inverse Laplacian operation to the Laplacian of phase.

According to the present invention, when phase restoration is performed by using an approximate expression on the basis of an image signal representing radiation image information obtained by X-ray imaging or the like, the image signal in which high spatial frequency components are suppressed or removed is used. Therefore, the phase restoration with high accuracy can be performed.

BRIEF DESCRIPTION OF THE DRAWINGS

FIG. 1 is a block diagram showing a construction of an X-ray imaging system including a phase information restoring apparatus according to one embodiment of the present invention;

FIG. 2 is a schematic view showing a construction of an imaging unit as shown in FIG. 1;

FIG. 3 is a flow chart showing a phase information restoring method according to one embodiment of the present invention;

FIGS. 4A–4E are views for explaining an LPF processing in frequency space;

DESCRIPTION OF THE PREFERRED EMBODIMENTS

Figures 5A, 5B, 5C, 5D, 5E:
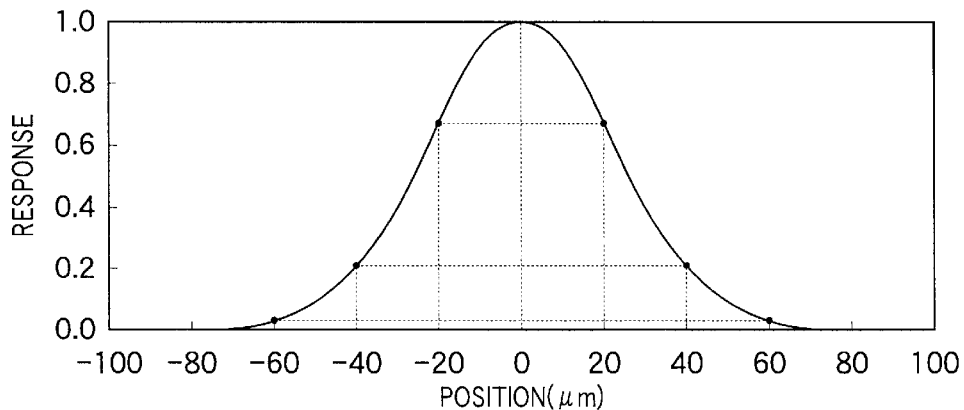
FIGS. 5A–5E are views for explaining an LPF processing in real space.

Embodiments of the present invention will be described in detail below by referring to the drawings. The same constituent elements will be given with the same reference numerals and the descriptions thereof will be omitted.

FIG. 1 is a block diagram showing an X-ray imaging system including a phase information restoring apparatus according to one embodiment of the present invention. The X-ray imaging system has an imaging unit 1 for irradiating X-rays on an object to be inspected so as to output image signals representing radiation image information about the object, a phase information restoring apparatus 2 for restoring phase information on the basis of the image signals, a display unit 3 for displaying a visible image on the basis of the restored phase information, and an output unit 4 for printing out a visible image on a film or the like.

FIG. 2 is a schematic view showing a construction of the imaging unit 1. As for a radiation source 11, a radiation source generating a radiation beam having high coherency and high monochromaticity is preferably used. Here, the beam having high monochromaticity means a beam mainly having a single wavelength. Accordingly, in this embodiment, a synchrotron radiation source for generating X-rays is used as the radiation source 11. The synchrotron radiation means the electromagnetic wave generated by accelerating an electron or bending a traveling direction of the electron. The X-rays generated by the radiation source 11 transmit through an object 10 and enter a sensor 12.

The sensor 12 detects incident X-rays. As for the sensor 12, a two-dimensional sensor having a plurality of detecting elements, which convert intensity of the irradiated radiation or synchrotron radiation into an electric signal to output the electric signal as a detection signal, such as a CCD (charge-coupled device) for example, is used. The detection signal output from the sensor 12 is amplified by an amplifier 15, converted into a digital signal (referred to as "image signal" or "detection data") by an A/D converter 16, and output into the phase information restoring apparatus 2.

The sensor 12 is held by a holding portion 13. The holding portion 13 can move on a rail 14. The holding portion 13 is controlled by a control unit 26 of the phase information restoring apparatus 2, which will be described later, and changes distance between the object 10 and the sensor 12 under the control of the control unit 26. Hereinafter, the distance between the object 10 and the sensor 12 is referred to as an imaging distance.

Referring again to FIG. 1, the phase information restoring apparatus 2 includes a storage unit 21 for temporarily storing the detection data output from the imaging unit 1, a differential processing unit 22 for obtaining a differential signal representing the difference between the detection data having different imaging distances, a low pass filter (LPF) 23 for performing a filter processing to the detection data, a phase restoring unit 24 for performing an arithmetic processing to restore the phase on the basis of the detection data, an image processing unit 25 for generating image data on the basis of the restored phase information, and the control unit 26 for controlling the respective units 21–25 and the imaging distance in the imaging unit 1. The phase information restoring apparatus 2 may further include a recording medium 27 for recording a phase information restoring program for actuating the respective units 21–25 to execute a predetermined processing. The phase information restoring apparatus 2 may be constituted of a digital circuit, or of software and a CPU. In the latter case, the control unit 26 including the CPU processes the detection data on the basis of the phase information restoring program recorded in the recording medium 27. As the recording medium 27, a flexible disk, hard disk, MO, MT, RAM, CD-ROM, DVD-ROM and so on are applicable.

The display unit 3 is, for example, a display device such as a CRT and displays a visible image on the basis of the image data representing the phase information restored by the phase information restoring apparatus 2. The output unit 4 is, for example, a laser printer and prints out a visible image on a film or the like on the basis of the image data.

Next, the description will be made on the principle of a phase information restoring method according to the present invention. The phase information restoring method according to the present invention is a method to be used for constructing a visible image in accordance with the phase contrast method, in which the phase restoration is performed by using the basic equation TIE (transport of intensity equation) of the phase restoration on the basis of plural diffraction fringe images obtained about an object. On that occasion, the method is characterized in that the detection data representing the diffraction fringe image information is subjected to a processing of suppressing or removing high spatial frequency components. Here, the reason why the detection data is subjected to such a processing is described.

An expression (6) is obtained by transforming the TIE represented by the following expression (5).

$$-\kappa \frac{\partial I(x, y)}{\partial z} = \nabla \cdot \{I(x, y) \nabla \phi(x, y)\} \tag{5}$$

$$-\kappa \frac{\partial I(x, y)}{\partial z} = I(x, y) \nabla^2 \phi(x, y) + \nabla I(x, y) \cdot \nabla \phi(x, y) \tag{6}$$

Here, I(x,y) is detection data representing diffraction light intensity at a position (x,y) on a plane at distance z from an object.

In the expression (6), when the right side second term $\nabla I(x,y) \cdot \nabla \phi(x,y)$ is approximated to zero, a TIE approximate expression (7) can be obtained.

$$\frac{\partial I(x, y)}{\partial z} \cong -\frac{I(x, y)}{\kappa} \nabla^2 \phi(x, y) \tag{7}$$

Here, in the case where a gradient $\nabla I(x,y)$ of the detection data I(x,y) is large, that is, in the case where high frequency components are contained in the detection data I(x,y), a value of the right side second term in the expression (6) increases and, as a result, accuracy of the TIE approximate expression (7) deteriorates. Consequently, by approximating the right side second term $\nabla I(x,y) \cdot \nabla \phi(x,y)$ in the expression (6) to zero by performing a process of cutting the high frequency components of the detection data I(x,y), the accuracy of the TIE approximate expression (7) can be enhanced.

$$\frac{\partial I(x, y)}{\partial z} = -\frac{I_{LPF}(x, y)}{\kappa} \nabla^2 \phi(x, y) \quad (8)$$

Here, $I_{LPF}(X,Y)$ represents the detection data I(x,y) where the high frequency components are cut.

Incidentally, when the detection data I(x,y) does not contain the high frequency components, the expression (8) can be directly derived from the TIE represented by the expression (5).

$$\frac{\partial I(x, y)}{\partial z} = -\frac{1}{\kappa} I_{LPF}(x, y) \nabla \cdot \nabla \phi(x, y) \quad (9)$$
$$= -\frac{I_{LPF}(x, y)}{\kappa} \nabla^2 \phi(x, y)$$

In this embodiment, the low pass filter (LPF) processing by a digital operation is performed in order to suppress or remove the high spatial frequency components in the detection data.

Next, referring to FIGS. 1–3, a phase information restoring method according to one embodiment of the present invention will be described. FIG. 3 is a flow chart showing the phase information restoring method according to one embodiment of the present invention. In this embodiment, a visible image is constructed by using two sheets of diffraction fringe images which are imaged by altering the imaging distance.

First, at step S1, the X-ray imaging is performed. More specifically, as shown in FIG. 2, the sensor 12 is disposed at an imaging distance of $z_1$ and X-rays are irradiated on the object 10, thereby performing the X-ray imaging. Subsequently, the sensor 12 is moved to be disposed at an imaging distance of $z_2$ and the X-ray imaging is performed in the same manner, thereby the diffraction fringe image information can be obtained.

By the X-ray imaging at step S1, the detection data $I_1(x,y)$ and $I_2(x,y)$ are input into the phase information restoring apparatus 2. Here, the detection data $I_1(x,y)$ represents diffraction light intensity at a position (x,y) on a plane at the imaging distance of $z_1$ and the detection data $I_2(x,y)$ represents diffraction light intensity at the position (x,y) on a plane at the imaging distance of $z_2$. The detection data $I_1(x,y)$ and $I_2(x,y)$ are sequentially stored in the storage unit 21 of the phase information restoring apparatus 2.

Next, at steps S2–S5, the phase information restoring apparatus 2 restores phase of the radiation on the basis of the detection data $I_1(x,y)$ and $I_2(x,y)$ stored in the storage unit 21.

First, at step S2, the differential processing unit 22 obtains a differential coefficient between the detection data $I_1(x,y)$ and $I_2(x,y)$ by using a following expression (10).

$$\frac{\partial I(x, y)}{\partial z} = \frac{I_2(x, y) - I_1(x, y)}{z_2 - z_1} \quad (10)$$

A value of the differential coefficient $\partial I(x,y)/\partial z$ is used as a differential signal in a later process.

Next, at step S3, the LPF 23 subjects the detection data to an LPF processing to obtain the detection data $I_{LPF}(X,Y)$ where the high spatial frequency components are suppressed or removed. As for the image information to be used for obtaining the detection data $I_{LPF}(x,y)$, the detection data $I_1(x,y)$ or the detection data $I_2(x,y)$ may be used, or the detection data obtained at a position other than the imaging distance of $z_1$ or $z_2$ may be used.

Here, the LPF processing will be described in detail. The LPF processing is a processing of extracting the low spatial frequency component in the detection data and may be performed in either a frequency space or a real space. In the following description, the detection data to be subjected to the LPF processing is referred to as $I_N$ and the resulting detection data is referred to as $I_N'$. Further, for simplicity, the detection data $I_N$ is presumed as one-dimensional image data including N pixel data arranged in one dimension.

(1) A method of performing filtering in the frequency space

FIGS. 4A–4E are views for explaining a method of performing the filtering in the frequency space. Here, as an example, the processing is performed by using a filter having Gaussian distribution as shown in FIG. 4A. Further, as shown in FIG. 4B, N pixel data included in the detection data $I_N$ are represented as I(0), I(1), . . . I(N−1). A sampling interval is D(m).

First, Fourier transform is performed to the detection data $I_N$. FIG. 4C shows the pixel data I'(0),I(1)', . . . I'(N−1) after Fourier transform. The sampling interval after Fourier transform is 1/ND (cycle/m).

Next, on the basis of the graph as shown in FIG. 4A, a digital filter is produced at the sampling intervals of 1/ND (cycle/m). For example, in the case of N=1024 and D=5μm, 1/ND 32 0.195 (cycle/mm) and the graph as shown in FIG. 4A is sampled at intervals of 0.195 (cycle/mm), thereby filter values of fil (0) to fil (N−1) as shown in FIG. 4D are obtained. In order to perform the LPF processing at a high speed, the filter is preferably produced in advance.

Next, an operation represented by the following expression is performed to every pixel. Here, g(n) represents value of the filtered pixel data.

$$g(n) = I'(n) \times \text{fil}(n)$$

where n=0, 1, . . . , N−1

FIG. 4E shows the pixel data of g(1) to g(N−1) obtained by the operation.

Further, an inverse Fourier transform is performed to data constituted by the pixel data of g(0) to g(N−1). By this operation, the detection data $I_N'$, which has been LPF processed, is obtained.

(2) A method of performing filtering in the real space

FIGS. 5A–5E are views for explaining a method of performing the filtering in the real space. FIG. 5A is a view showing a real space filter obtained by performing an inverse Fourier transform to the filter having the Gaussian distribution as shown in FIG. 4A. FIG. 5B shows N pixel data of I(0), I(1), . . . , I(N−1) which constitute the detection data $I_N$. The sampling interval is D(m).

First, the real space filter is produced on the basis of the graph as shown in FIG. 5A. More specifically, the graph as shown in FIG. 5A is sampled at the sampling interval of D(m) and response values obtained are normalized such that the sum of filter values in the whole filter becomes 1, thereby the filter values of fil'(−M+1) to fil'(M−1) as shown in FIG. 5C can be obtained. Here, in FIG. 5C, M=N/2.

In the case of D=20 μm for example, by taking responses at the sampling points of 0 μm, ±20 μm, ±40 μm and ±60 μm in the graph as shown in FIG. 5A, the values corresponding to the respective pixels can be obtained as shown in FIG. 5D. Further, when these values are normalized, the filter values of fil'(−M+1) to fil'(M−1) as shown in FIG. 5E can be obtained.

Next, a convolution operation represented by a following expression (11) is performed to the pixel data as shown in FIG. 5B. Here, g(n) represents a value of the filtered pixel data. The symbol * represents the convolution operation.

$$g(n) = f(n) * I(n) = \sum_{k=-M+1}^{M-1} f(k)I(n-k) \quad (11)$$

Thus obtained pixel data of g(0) to g(N−1) constitute the detection data $I_N'$ that have been LPF processed.

Referring again to FIG. 3, at step S4, the phase restoring unit 24 obtains Laplacian $f(x,y)=\nabla^2\phi(x,y)$ of phase by using a following expression (12) based on the differential signal obtained at step S2 and the detection data $I_{LPF}(x,y)$ obtained at step S3.

$$f(x, y) = -\frac{k}{L_{LPF}(x, y)} \frac{\partial I(x, y)}{\partial z} \quad (12)$$

Further, at step 5, the phase restoring unit 24 performs an inverse Laplacian operation to the Laplacian f(x,y) of phase, which has been obtained at step S4, so as to obtain the phase ϕ(x,y) of the radiation.

Here, the inverse Laplacian operation will be described in detail. The Fourier transform of f(x,y) is represented as a following expression (13).

$$F[f(x,y)] = F[\nabla^2\phi(x,y)]$$
$$= -4\pi^2(u^2+v^2)F[f(x,y)] \quad (13)$$

where F[ ] represents Fourier transform and u, v are spatial frequencies corresponding to x, y respectively.

Accordingly, the phase ϕ(x,y) is represented as a following expression (14).

$$\phi(x, y) = F^{-1}\left[-\frac{1}{4\pi^2(u^2+v^2)} F[f(x, y)]\right] \quad (14)$$

Here, $F^{-1}[\ ]$ represents inverse Fourier transform.

By utilizing the expression (14), inverse Laplacian operation can be performed. Specifically, f(x,y) is Fourier transformed, then multiplied by $\{-4\pi^2(u^2+v^2)\}^{-1}$ and the product is further inverse Fourier transformed to obtain the restored phase ϕ(x,y).

Here, a value of $\{-4\pi^2(u^2+v^2)\}^{-1}$ may be previously calculated within a range, where each of |u| and |v| is not larger than a predetermined value, so that the previously calculated value can be utilized in performing the operation represented by the expression (14). In other words, a predetermined value "const" is set and in the case where |u|, |v|≦const, a value of the following expression is used in the expression (14).

$$\{-4\pi^2(u^2+v^2)\}^{-1} = \text{(the previously calculated value)}$$

On the other hand, in the case where |u|, |v|>const, a value of the following expression is used in the expression (14).

$$\{-4\pi^2(u^2+v^2)\}^{-1} = 0$$

By virtue of this, inverse Laplacian operation can be performed at a high speed.

Next, at step S6, the image processing unit 25 generates image data on the basis of the restored phase ϕ(x,y). Specifically, the image processing unit 25 converts the phases ϕ(x,y) in the respective pixels into the image data showing brightness, and then, performs a necessary image processing such as a gradation processing or an interpolation processing to the image data.

At step S7, the display unit 3 or the output unit 4 displays a visible image on a screen, a film or the like on the basis of thus generated image data.

Incidentally, in this embodiment, the LPF processing is performed by the operation as described above in order to suppress or remove the high spatial frequency components in the detection data. However, any other processing may be performed as long as the high spatial frequency components can be suppressed or removed. Examples of such a processing include a statistical filter processing such as a Median filter processing, a Morphological operation and a high degree polynomial approximate processing. Further, the LPF processing may be performed at the stage of an analogue signal before digitization of the detection signal.

In this embodiment, such method is described that the phase is restored on the basis of two sheets of interference fringe images imaged by altering the imaging distance. Alternatively, the phase may also be restored using three or more sheets of interference fringe images.

Further, in this embodiment, although X-rays are used for imaging an object, not only X-rays but also any other beams may be used as long as the beam transmits through the object to form a diffraction figure. As for such a beam, for example, a corpuscular beam including an electron beam can be mentioned.

In this embodiment, although the synchrotron radiation source is used for imaging an object, a radiation source generating a beam that is not the synchrotron radiation may be used. For example, a high-brightness hard X-ray generation apparatus of an electronic accumulative type developed by Ritsumeikan University can generate X-rays having high luminance and directivity just like the synchrotron radiation in spite of a desktop apparatus. X-rays generated by the apparatus have coherency and also can be rendered monochromatic by combination with a monochromatizing crystal though they have not a single wavelength. Also, a radiation source developed by the Femtosecond Technology Research Association (FESTA) generates ultrashort pulse high-brightness X-rays on the basis of the principle of inverse Compton scattering. The radiation source is compact and portable, and can generate the X-rays having not only coherency but also high directivity and monochromaticity. When a point source of radiation is used as the radiation source, it is preferable to correct magnification and so on at the time of data processing in the phase information restoring apparatus.

Figure 6:
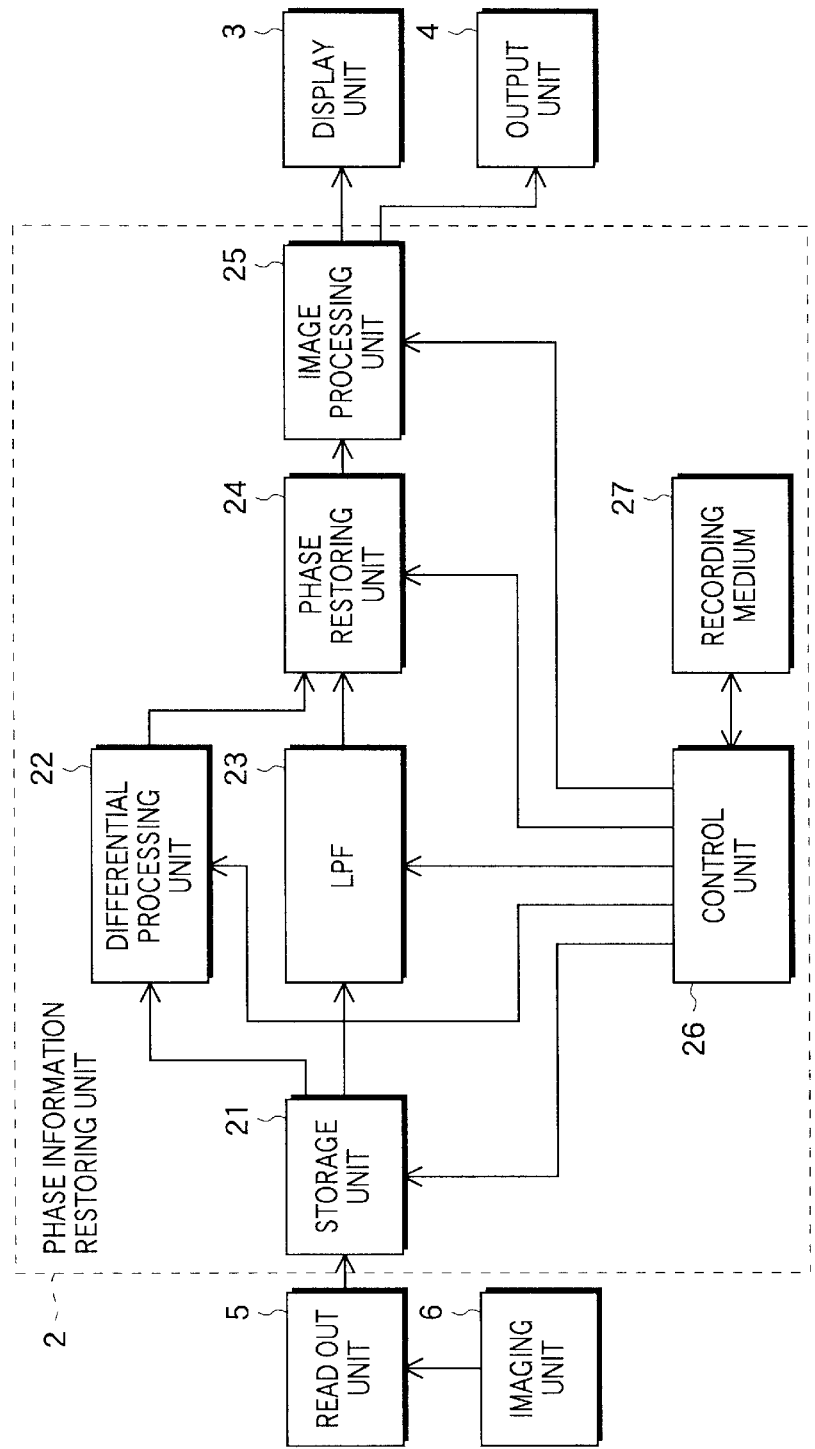
FIG. 6 is a block diagram showing a modified example of an X-ray imaging system including a phase information restoring apparatus according to one embodiment of the present invention.

Next, referring to FIG. 6, a modified example of an X-ray imaging system including the phase information restoring apparatus according to the one embodiment of the present invention will be explained. The X-ray imaging system as shown in FIG. 6 has a read unit 5 and an imaging unit 6. Other constructions are similar to those of the X-ray imaging system as shown in FIG. 1.

In the imaging unit 6, as for a screen to be used for recording the image information, a photostimulable phosphor sheet (record sheet) is used in place of the sensor 12 in the imaging unit 1 as shown in FIG. 2.

The photostimulable phosphor (accumulative phosphor) is substance that, when irradiated by a radiation, accumulates a part of the radiation energy and that, when an excitation light such as visible light is then irradiated, emits stimulated fluorescence corresponding to the accumulated energy. When a radiation image of an object such as a human body is imaged and recorded on a sheet coated with the photostimulable phosphor and the photostimulable phosphor sheet is scanned by the excitation light such as laser light, stimulated fluorescence is generated. By photoelectrically reading out the light, the detection data can be obtained. The detection data is appropriately processed and output to a display such as a CRT or output to a laser printer for printing an image on a film, so that the radiation image can be displayed as a visible image.

The read unit 5 as shown in FIG. 6 is used for reading out the radiation image recorded in the record sheet.

Figure 7:
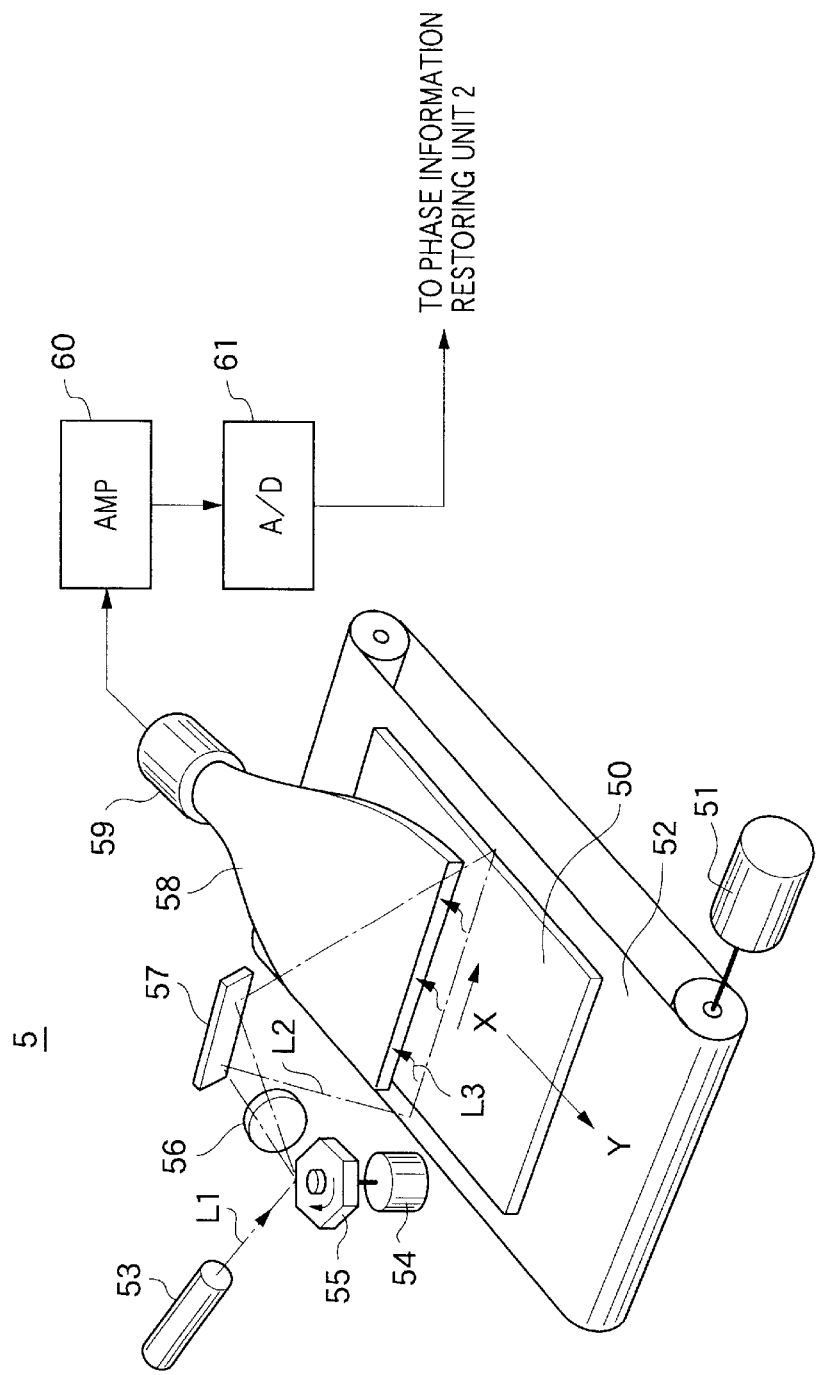
FIG. 7 is a schematic view showing a construction of a reading unit as shown in FIG. 6.
Figure 8:
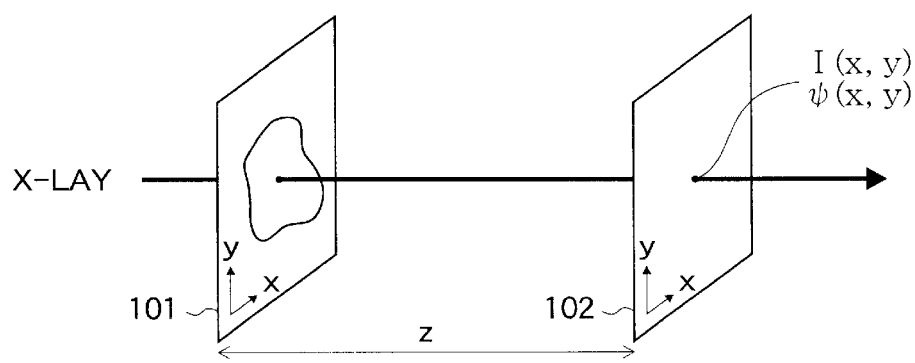
FIG. 8 is a view for explaining the principle of the phase restoration.

Referring to FIG. 7, construction and operation of the read unit 5 will be explained. The record sheet 50, on which the image information has been recorded, is set in a predetermined position of the read unit 5. The record sheet 50 is carried in the Y direction indicated by an arrow with a sheet carrier unit 52 driven by a motor 51. On the other hand, a beam L1 oscillated from a laser light source 53 is reflected and deflected by a rotational polygon mirror 55 which is driven by a motor 54 to rotate at a high speed in the direction indicated by an arrow and passes through a convergent lens 56. Then, the beam L1 is forced to change a light path by a mirror 57 and scans the record sheet 50 in the X direction indicated by an arrow. By the scanning, excitation light L2 is irradiated on the record sheet 50 and from an irradiated part, stimulated fluorescent light L3 having a light volume corresponding to the radiation image information accumulated and recorded is emitted. The stimulated fluorescent light L3 is guided by a light guide 58 and photoelectrically detected by a photomultiplier 59. An analogue signal output from the photomultiplier 59 is amplified by an amplifier 60 and digitized by an A/D converter 61. A digital signal output from the A/D converter 61 is input into the phase information restoring apparatus 2.

The imaging unit 6 performs radiation imaging by using a plurality of record sheets while altering the imaging distance, and the read unit 5 reads out the image information from the respective record sheets. As a result, a plurality of image signals representing diffraction fringe image information obtained at different imaging distances can be obtained. The phase information restoring apparatus 2 restores the phase of the radiation on the basis of these image signals. The processing in the phase information restoring apparatus 2 is similar to that shown in FIG. 3.

As described above, according to the present invention, the image signal, in which high spatial frequency components are suppressed or removed, is used in the TIE approximate expression, and therefore, the phase restoration ensuring high accuracy can be performed. Accordingly, it becomes possible to obtain a visualized X-ray image having high image quality by using the phase contrast method.

What is claimed is:

1. A method of restoring phase information of radiation transmitted through an object on the basis of a plurality of image signals respectively obtained by detecting intensity of radiation transmitted through the object on a plurality of planes different in distance from the object, each of the plurality of image signals representing radiation image information on the plurality of planes, said method comprising the steps of:

obtaining a differential signal representing difference between a first image signal and a second image signal of said plurality of image signals;

subjecting any one of said plurality of image signals to one of a suppressing process and a removing process for high spatial frequency components thereof so as to generate a third image signal;

obtaining Laplacian of phase with respect to said differential signal and said third image signal; and restoring phase information of the radiation by applying an inverse Laplacian operation to said Laplacian of phase.

2. An apparatus for restoring phase information of radiation transmitted through an object on the basis of a plurality of image signals respectively obtained by detecting intensity of radiation transmitted through the object on a plurality of planes different in distance from the object, each of the plurality of image signals representing radiation image information on the plurality of planes, said apparatus comprising:

differential signal generating means for obtaining a differential signal representing difference between a first image signal and a second image signal of said plurality of image signals;

signal processing means for subjecting any one of said plurality of image signals to one of a suppressing process and a removing process for high spatial frequency components thereof so as to generate a third image signal;

phase restoring means for obtaining Laplacian of phase with respect to said differential signal and said third image signal, and restoring phase information of the radiation by applying an inverse Laplacian operation to said Laplacian of phase.

3. A phase information restoring program for restoring phase information of radiation transmitted through an object on the basis of a plurality of image signals respectively obtained by detecting intensity of radiation transmitted through the object on a plurality of planes different in distance from the object, each of the plurality of image signals representing radiation image information on the plurality of planes, said program actuating a CPU to execute the procedures of:

obtaining a differential signal representing difference between a first image signal and a second image signal of said plurality of image signals;

subjecting any one of said plurality of image signals to one of a suppressing process and a removing process for high spatial frequency components thereof so as to generate a third image signal;

obtaining Laplacian of phase with respect to said differential signal and said third image signal; and restoring phase information of the radiation by applying an inverse Laplacian operation to said Laplacian of phase.

* * * * *